(12) United States Patent
Stote

(10) Patent No.: US 11,457,625 B1
(45) Date of Patent: Oct. 4, 2022

(54) TUNING A BROAD ACTING ANTIMICROBIAL TEXTILE TO ACT AS A NARROW SPECTRUM ANTIMICROBIAL TEXTILE

(71) Applicant: U.S. Government as Represented by the Secretary of the Army, Natick, MA (US)

(72) Inventor: Robert E Stote, Pepperell, MA (US)

(73) Assignee: U.S. Government as Represented by the Secretary of the Army, Washington, DC (US)

(*) Notice: Subject to any disclaimer, the term of this patent is extended or adjusted under 35 U.S.C. 154(b) by 420 days.

(21) Appl. No.: 16/597,886

(22) Filed: Oct. 10, 2019

Related U.S. Application Data

(60) Provisional application No. 62/760,083, filed on Nov. 13, 2018.

(51) Int. Cl.
| | | |
|---|---|---|
| *D06M 16/00* | (2006.01) | |
| *C07K 7/08* | (2006.01) | |
| *A01N 25/34* | (2006.01) | |
| *A01N 47/40* | (2006.01) | |

(52) U.S. Cl.
CPC ............. *A01N 25/34* (2013.01); *A01N 47/40* (2013.01); *C07K 7/08* (2013.01); *D06M 16/00* (2013.01)

(58) Field of Classification Search
CPC .................................. C07K 7/08; D06M 16/00
See application file for complete search history.

(56) References Cited

U.S. PATENT DOCUMENTS

2004/0137482 A1* 7/2004 Eckert ................ C12N 15/8258
435/6.15

FOREIGN PATENT DOCUMENTS

WO WO-2010080819 A1 * 7/2010 ............ A01N 37/46

OTHER PUBLICATIONS

Gomes et al. Incorporation of antimicrobial peptides on functionalized cotton gauzes for medical applications, Carbohydrate Polymers, vol. 127, 2015, pp. 451-461, https://doi.org/10.1016/j.carbpol.2015.03.089.*
Chindera et al. The antimicrobial polymer PHMB enters cells and selectively condenses bacterial chromosomes. Sci Rep 6, 23121 (2016). https://doi.org/10.1038/srep23121.*
Orlandin et al. (Cotton functionalized with peptides: characterization and synthetic methods. J Pept Sci Jul. 2014;20(7):547-53. doi:10.1002/psc.2659. Epub May 28, 2014.*
Elsner, Peter, "Antimicrobials and the Skin Physiological and Pathological Flora", Efficiency of Biofunctional Textiles, vol. 33, 2006, pp. 35-41.
Windler, Lena, et al., "Comparative evaluation of antimicrobials for textile applications", Environment International, Elsevier, vol. 53, Mar. 2013, pp. 62-73.
Larson, Elaine, "Hygiene of the Skin: When Is Clean Too Clean?", Special Issue, Emerging Infectious Diseases, vol. 7, No. 2, Mar.-Apr. 2001, pp. 225-230.
Walter, Nancy, et al., "In vivo assessment of antimicrobial-treated textiles on skin microflora", International Journal of Clothing Science and Technology, vol. 26, No. 04, 2014, pp. 330-342.
McQueen, Rachel H., et al., "Reducing laundering frequency to prolong the life of denim jeans", International Journal of Consumer Studies, vol. 41, 2017, pp. 36-45.

* cited by examiner

*Primary Examiner* — Gregory S Emch
(74) *Attorney, Agent, or Firm* — Roger C Phillips

(57) ABSTRACT

The disclosed subject matter relates to a textile or fabric and methods of making them that includes a composition that selectively binds odor causing and/or pathogenic bacteria, but avoids binding beneficial bacteria and an antimicrobial composition that kills the selectively bound odor causing and/or pathogenic bacteria. The composition that selectively binds odor causing and/or pathogenic bacteria can be a peptide.

7 Claims, 4 Drawing Sheets
Specification includes a Sequence Listing.

Salivaricin 9
GNGVVLTLTHECNLATWTKKLKCC

Mutacin H-29B
NRWWQGVVPTVSYECRMNSWQHVFTCC

Cerein 7B
GWWNSWGKCVAGTIGGAGTGGLGGAAAGSAVPVIGTGIGGAIGGVSGGLTGAATFC

```
                        SEQUENCE LISTING

<160> NUMBER OF SEQ ID NOS: 9

<210> SEQ ID NO 1
<211> LENGTH: 12
<212> TYPE: PRT
<213> ORGANISM: MICROCOCCUS LUTEUS and CORYNEBACTERIUM JEIKIEUM

<400> SEQUENCE: 1

Gly Gly Ser Gly Gly Asn Gly Val Val Leu Thr Leu
1               5                   10

<210> SEQ ID NO 2
<211> LENGTH: 12
<212> TYPE: PRT
<213> ORGANISM: MICROCOCCUS LUTEUS and CORYNEBACTERIUM JEIKIEUM

<400> SEQUENCE: 2

Gly Gly Ser Gly Gly Thr Trp Thr Lys Lys Leu Lys
1               5                   10

<210> SEQ ID NO 3
<211> LENGTH: 14
<212> TYPE: PRT
<213> ORGANISM: MICROCOCCUS LUTEUS and CORYNEBACTERIUM JEIKIEUM

<400> SEQUENCE: 3

Gly Gly Ser Gly Gly Asn Arg Trp Trp Gln Gly Val Val Pro
1               5                   10

<210> SEQ ID NO 4
<211> LENGTH: 12
<212> TYPE: PRT
<213> ORGANISM: MICROCOCCUS LUTEUS and CORYNEBACTERIUM JEIKIEUM

<400> SEQUENCE: 4

Gly Gly Ser Gly Gly Ser Trp Gln His Val Phe Thr
1               5                   10

<210> SEQ ID NO 5
<211> LENGTH: 15
<212> TYPE: PRT
<213> ORGANISM: MICROCOCCUS LUTEUS and CORYNEBACTERIUM JEIKIEUM

<400> SEQUENCE: 5

Gly Gly Ser Gly Gly Gly Trp Trp Asn Ser Trp Gly Lys Cys Val
1               5                   10                  15

<210> SEQ ID NO 6
<211> LENGTH: 15
<212> TYPE: PRT
<213> ORGANISM: MICROCOCCUS LUTEUS and CORYNEBACTERIUM JEIKIEUM

<400> SEQUENCE: 6

Gly Gly Ser Gly Gly Ile Gly Gly Val Ser Gly Gly Leu Thr Gly
1               5                   10                  15
```

```
<210> SEQ ID NO 7
<211> LENGTH: 14
<212> TYPE: PRT
<213> ORGANISM: STAPHYLOCOCCUS AUREUS

<400> SEQUENCE: 7

Gly Gly Ser Gly Gly Ser Tyr Ser Thr Cys Asp Phe Ile Met
1               5                   10

<210> SEQ ID NO 8
<211> LENGTH: 18
<212> TYPE: PRT
<213> ORGANISM: PSEUDOMONAS AERUGINOSA

<400> SEQUENCE: 8

Gly Gly Ser Gly Gly Ser Lys Lys His Arg Lys His Arg Lys His Arg
1               5                   10                  15

Lys His

<210> SEQ ID NO 9
<211> LENGTH: 14
<212> TYPE: PRT
<213> ORGANISM: STAPHYLOCOCCUS AUREUS

<400> SEQUENCE: 9

Gly Gly Ser Gly Gly Ser Tyr Ser Thr Cys Tyr Phe Ile Met
1               5                   10
```

TUNING A BROAD ACTING ANTIMICROBIAL TEXTILE TO ACT AS A NARROW SPECTRUM ANTIMICROBIAL TEXTILE

CROSS-REFERENCE TO RELATED APPLICATIONS

This application claims priority to and the benefit of U.S. Provisional Patent Application Ser. No. 62/760,083 filed Nov. 13, 2018, the disclosure of which is incorporated herein by reference in its entirety.

STATEMENT OF GOVERNMENT INTEREST

The invention described herein may be manufactured and used by or for the U.S. Government for governmental purposes without the payment of any royalties thereon or therefor.

FIELD

The aspects of the present disclosure relate to textiles, compositions and method including antimicrobial textiles.

BACKGROUND

Laundering textiles causes significant degradation through the physical breakdown of fibers during the wash cycles. This significantly decreases the longevity of the textile and decreases added capabilities. Composite uniforms such as the chemical protective, the bomb-blast and the cooling suits, are especially susceptible as the different active layers degrade with laundering. Reducing or eliminating the need to wash the materials have been an Army goal for a few years (McQueen, Rachel H., Jane C. Batcheller, Lori J. Moran, Han Zhang, and Peter M. Hopper. "Reducing Laundering Frequency to Prolong the Life of Denim Jeans." *International Journal of Consumer Studies."* 41(2017):36-45). Malodor is the primary reason the Army washes uniforms so reducing odor by adding antimicrobial to textiles has been a focus. Though this approach has been effective at reducing odor, there are concerns that the currently used broad acting antimicrobials may affect skin microbiome health (Windler, Lena, Murray Height, and Bernd Nowack. "Comparative evaluation of antimicrobials for textile applications." *Environment International.* 53(2013):62-73).

There is convincing results supporting the hypothesis that using broad acting antimicrobials is problematic. Broad acting antimicrobials act indiscriminately and prolonged contact by these antimicrobial textiles leads to lower totals counts for skin bacteria (Elsner, P. "Antimicrobials and the Skin Physiological and Pathological Flora". *Current Problems in Dermatiology.* 33(2006):35-41; Walter, Nancy, Rachel H. McQueen, and Monika Keelan. "In vivo assessment of antimicrobial-treated textiles on skin microflora." *International Journal of Clothing Science and Technology* 26.4 (2014): 330-342). Related studies have also shown that use of broad spectrum anitmicrobials can result in the loss of beneficial skin bacteria, thus increasing the risk of skin irritation, rashes and dermatitis (Elaine Larson, "Hygiene of the skin: when is clean too clean?" *Emerging infectious diseases,* 7(2),). Long term use of broad spectrum antimicrobials may also result in other unknown health impacts. A better approach would be to use targeted or narrow spectrum antimicrobials on textiles instead of the broad acting.

Early efforts at developing targeted antimicrobials looked at Bacteriocins, small peptides produced by bacteria to kill competing bacteria. They are very specific and will only affect a small number of species. Isolated bacteriocins which targeted pathogenic bacteria were encapsulated in metal oxide bound to the surface of textiles. Although, the encapsulated bacteriocins retained activity, the encapsulated bacteriocins lost activity quickly due to leaching of the bacteriocins and instability of the encapsulated bacteriocin.

Targeted antimicrobials such as bacteriocin and phage can be composed of regions or modules which each have a specific function. One module may allow the antimicrobial to pass through a cell membrane, while a second region may act as the killing component of the antimicrobial and a third region (the recognition sequence) can act as the targeting mechanism. The latter region can be a short peptide sequence that binds to specific elements on the surface of the target bacteria. Replacing the recognition sequence with a sequence that would bind a different bacteria, can switch the activity toward the new bacteria. However, there are still issues with leaching when encapsulated and activity loss when covalently bonded to a surface.

It would be desirable to have an antimicrobial textile that is narrow acting to avoid killing the beneficial bacteria while targeting the odor causing and/or pathogenic bacteria and would maintain its effectiveness for longer periods of time.

DESCRIPTION OF THE DRAWINGS

The accompanying drawings illustrate presently preferred embodiments of the present disclosure, and together with the general description given above and the detailed description given below, serve to explain the principles of the present disclosure.

SUMMARY

Figure 1:
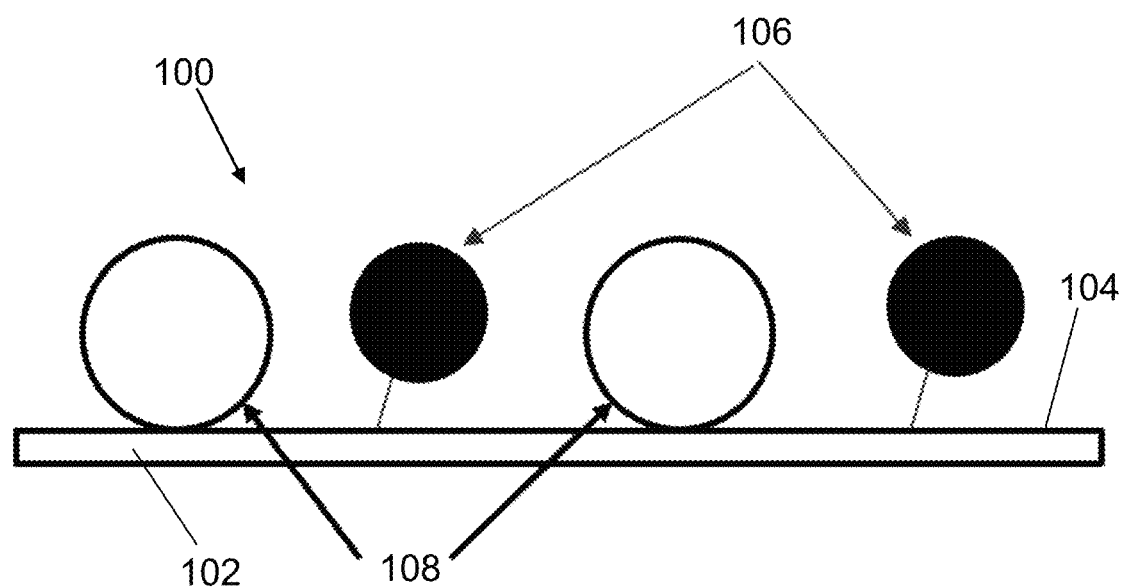
FIG. 1 is an exemplary illustration of an embodiment of the present disclosure.

In one embodiment, an antimicrobial fabric is provided. The antimicrobial fabric includes a fabric layer, an antimicrobial composition and a peptide, wherein the peptide is selected from the group consisting of:

```
                                             (SEQ ID NO: 7)
         GGSGGSYSTCDFIM;

(SEQ ID NO: 8)
         GGSGGSKKHRKHRKHRKH;
```

GGSGGNGVVLTL; (SEQ ID NO: 1)

GGSGGTWTKKLK; (SEQ ID NO: 2)

GGSGGNRWWQGVVP; (SEQ ID NO: 3)

GGSGGSWQHVFT; (SEQ ID NO: 4)

GGSGGGWWNSWGKCV; (SEQ ID NO: 5)

GGSGGIGGVSGGLTG; (SEQ ID NO: 6)
and

GGSGGSYSTCYFIM. (SEQ ID NO: 9)

In another embodiment, an antimicrobial fabric is provided. The antimicrobial fabric including a fabric layer, a peptide that selectively binds to at least one bacteria selected from the group consisting of *Staphylococcus aureus, Pseudomonas aeruginosa, Corynebacterium* and *Micrococcus luteus*, wherein the peptide is selected from the group consisting of:

GGSGGSYSTCDFIM; (SEQ ID NO: 7)

GGSGGSKKHRKHRKHRKH; (SEQ ID NO: 8)

GGSGGNGVVLTL; (SEQ ID NO: 1)

GGSGGTWTKKLK; (SEQ ID NO: 2)

GGSGGNRWWQGVVP; (SEQ ID NO: 3)

GGSGGSWQHVFT; (SEQ ID NO: 4)

GGSGGGWWNSWGKCV; (SEQ ID NO: 5)

GGSGGIGGVSGGLTG; (SEQ ID NO: 6)
and

GGSGGSYSTCYFIM; and (SEQ ID NO: 9)

an antimicrobial composition that kills the at least one bacteria.

In another embodiment, a method of treating a fabric to selectively kill bacteria is provided. The method includes binding an antimicrobial composition and a peptide to the fabric, wherein the peptide is selected from the group consisting of:

GGSGGSYSTCDFIM; (SEQ ID NO: 7)

GGSGGSKKHRKHRKHRKH; (SEQ ID NO: 8)

GGSGGNGVVLTL; (SEQ ID NO: 1)

GGSGGTWTKKLK; (SEQ ID NO: 2)

GGSGGNRWWQGVVP; (SEQ ID NO: 3)

GGSGGSWQHVFT; (SEQ ID NO: 4)

GGSGGGWWNSWGKCV; (SEQ ID NO: 5)

GGSGGIGGVSGGLTG; (SEQ ID NO: 6)
and

GGSGGSYSTCYFIM. (SEQ ID NO: 9)

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

The terms "%", "% by weight", "weight %" and "wt %" are all intended to mean unless otherwise stated, percents by weight based upon a total weight of 100% end composition weight. Thus 10% by weight means that the component constitutes 10 wt. parts out of every 100 wt. parts of total composition.

Aspects of the present disclosure include a textile or fabric and methods of making them that includes a composition that selectively binds odor causing and/or pathogenic bacteria, but avoids binding beneficial bacteria and an antimicrobial composition that kills the selectively bound odor causing and/or pathogenic bacteria. The composition that selectively binds odor causing and/or pathogenic bacteria can be a peptide.

Instead of modifying an existing antimicrobial then binding the agent to a textile or fabric, a composition that selectively binds a specific bacteria, e.g., a recognition sequence (peptide), that the textile or fabric is designed to kill can be bound to the surface of an existing antimicrobial textile to tune these textiles to act as narrow spectrum only for specific bacteria that are not beneficial and not designed to bind bacteria that are beneficial. The key is to bind the peptide to the textile or fabric and not to the antimicrobial agent thereby leaving the antimicrobial activity intact.

FIG. 1 is illustrative of aspects of one embodiment of an antimicrobial fabric 100 of the present disclosure. Antimicrobial fabric 100 includes fabric layer 102 and an antimicrobial surface 104 of fabric layer 102. The fabric layer 102 can include, for example, fire resistant or non-fire-resistant materials, stretch or non-stretch fabrics, knit or woven fabric materials that can be, for example, aramid-based flame-resistant material, cotton, nylon, blends such as cotton blends and nylon/cotton blends, polyester or polyester blends. Antimicrobial surface 104 can be designed to face the external environment (e.g. the outside of the garment in which antimicrobial fabric 100 is used that can include sunlight, rain, and other external environmental conditions) can also optionally include a repellant coating, such as, for example, a liquid repellant coating (such as silica based liquid repellent coatings or perfluoronated carbon based liquid repellent coatings). Antimicrobial surface 104 can also be designed to face the internal environment (e.g. closer to the body of the wearer of a garment in which antimicrobial fabric 100 is used). Bound, e.g., chemically bound, to the antimicrobial surface 104 of fabric layer 102 is one or more compositions that selectively bind odor causing and/or pathogenic bacteria 106 and one or more antimicrobial compositions that kill the selectively bound odor causing and/or pathogenic bacteria 108.

Figure 2:
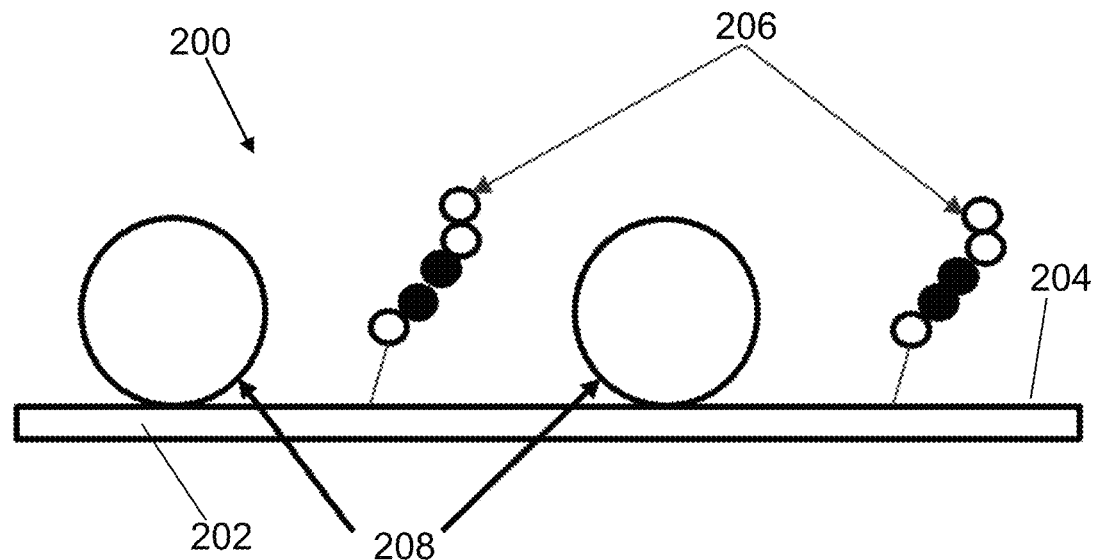
FIG. 2 is an exemplary illustration of an embodiment of the present disclosure.

FIG. 2 is illustrative of aspects of another embodiment of an antimicrobial fabric 200 of the present disclosure. Antimicrobial fabric 200 includes fabric layer 202 and an antimicrobial surface 204 of fabric layer 202. The fabric layer 202 can include, for example, fire resistant or non-fire-resistant materials, stretch or non-stretch fabrics, knit or woven fabric materials that can be, for example, aramid-based flame-resistant material, cotton, nylon, blends such as cotton blends and nylon/cotton blends, polyester or polyester blends. Antimicrobial surface 204 can be designed to face the external environment (e.g. the outside of the garment in which antimicrobial fabric 200 is used that can include sunlight, rain, and other external environmental conditions) can also optionally include a repellant coating, such as, for example, a liquid repellant coating (such as silica based liquid repellent coatings or perfluoronated carbon based liquid repellent coatings). Antimicrobial surface 104 can also be designed to face the internal environment (e.g. closer to the body of the wearer of a garment in which antimicrobial fabric 200 is used). Bound, e.g., chemically bound, to the antimicrobial surface 204 of fabric layer 202 is one or more peptides that selectively bind odor causing and/or pathogenic bacteria 206 and one or more antimicrobial compositions that kill the selectively bound odor causing and/or pathogenic bacteria 208.

Examples of the antimicrobial composition that kills the selectively bound odor causing and/or pathogenic bacteria (108 in FIGS. 1 and 208 in FIG. 2) can include but are not limited to polyhexamethylene biguanidine (PHMB), quaternary ammonium compounds, antimicrobial dyes, metals (silver, copper, zinc), etc.

Figures 3, 4A, 4B, 4C:
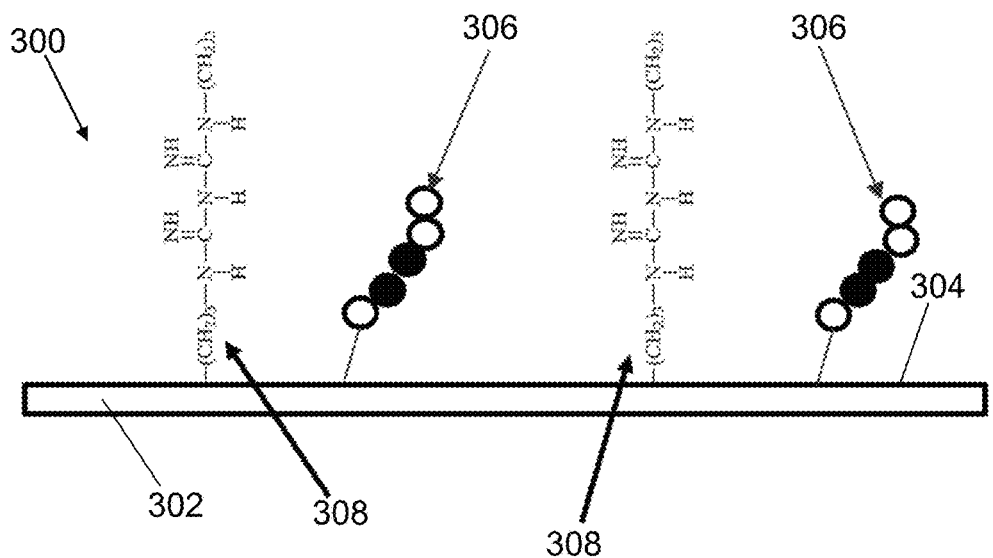
FIG. 3 is an exemplary illustration of an embodiment of the present disclosure.
FIG. 4A is an exemplary illustration of the sequence of Salivaricin 9.
FIG. 4B is an exemplary illustration of the sequence of Mutacin H-29B.
FIG. 4C is an exemplary illustration of the sequence of Cerein 7B.

FIG. 3 is illustrative of aspects of another embodiment of an antimicrobial fabric 300 of the present disclosure. Antimicrobial fabric 300 includes fabric layer 302 and an antimicrobial surface 304 of fabric layer 302. The fabric layer 302 can include, for example, fire resistant or non-fire-resistant materials, stretch or non-stretch fabrics, knit or woven fabric materials that can be, for example, aramid-based flame-resistant material, cotton, nylon, blends such as cotton blends and nylon/cotton blends, polyester or polyester blends. Antimicrobial surface 304 can be designed to face the external environment (e.g. the outside of the garment in which antimicrobial fabric 300 is used that can include sunlight, rain, and other external environmental conditions) can also optionally include a repellant coating, such as, for example, a liquid repellant coating (such as silica based liquid repellent coatings or perfluoronated carbon based liquid repellent coatings). Antimicrobial surface 304 can also be designed to face the internal environment (e.g. closer to the body of the wearer of a garment in which antimicrobial fabric 300 is used). Bound, e.g., chemically bound, to the antimicrobial surface 304 of fabric layer 302 is one or more peptides that selectively bind odor causing and/or pathogenic bacteria 306 and PHMB that kills the selectively bound odor causing and/or pathogenic bacteria 308.

Examples of the peptides that selectively bind odor causing and/or pathogenic bacteria (206 in FIGS. 2 and 306 in FIG. 3) can include those listed in Table 1. The microorganism recognized indicates the microorganism that that will selectively bind to the peptide.

TABLE 1

| Sequence synthesized | Microorganism recognized |
| --- | --- |
| GGSGGSYSTCDFIM (AgrD1 pheromone) | Staphylococcus aureus |
| GGSGGSKKHRKHRKHRKH | Pseudomonas aeruginosa |
| GGSGGNGVVLTL | Corynebacterium and Micrococcus luteus |
| GGSGGTWTKKLK | Corynebacterium and Micrococcus luteus |
| GGSGGNRWWQGVVP | Corynebacterium and Micrococcus luteus |
| GGSGGSWQHVFT | Corynebacterium and Micrococcus luteus |
| GGSGGGWWNSWGKCV | Corynebacterium and Micrococcus luteus |
| GGSGGIGGVSGGLTG | Corynebacterium and Micrococcus luteus |
| GGSGGSYSTCYFIM | Staphylococcus aureus |

The peptides in Table 1 includes sequences derived from bacteriocins that bind to the microorganism recognized that is identified in Table 1 and are synthesized by various providers of custom peptides including, for example, New England peptides in Gardner, Mass. The sequences in Table 1 include a linker sequence of GGSGG or GGSG depending on the peptide. The linker sequence is bound to the textile and serves to connect the peptide sequence to the textile. Some of the sequences in Table 1 were derived from the bacteriocin sequences included in Table 2.

TABLE 2

| Sequence | Origin |
| --- | --- |
| SYSTCDFIM | Autoinducing peptide produced by Staphylococcus aureus |
| SKKHRKHRKHRKH | Eckert, R., Qi, F., Yarbrough, D. K., He, J., Anderson, M. H., & Shi, W. (2006). Adding selectivity to antimicrobial peptides: rational design of a multidomain peptide against Pseudomonas spp. Antimicrobial agents and chemotherapy, 50(4), 1480-1488. |
| GNGVVLTL | Salivaricin 9 (a lantibiotic produced by Streptococcus alivarius) |
| TWTKKLK | Salivaricin 9 (a lantibiotic produced by Streptococcus alivarius) |
| NRWWQGVVP | Mutacin H-29B (a lantibiotic produced by S. mutans strain 29B) |
| SWQHVFT | Mutacin H-29B (a lantibiotic produced by S. mutans strain 29B) |
| GWWNSWGKCV | Cerein 7B (a bacteriocin produced by Bacillus cereus Bc7) |
| IGGVSGGLTG | Cerein 7B (a bacteriocin produced by Bacillus cereus Bc7) |
| SYSTCYFIM | Autoinducing peptide produced by Staphylococcus |

FIGS. 4A, 4B and 4C include the sequences of Salivaricin 9, Mutacin H-29B and Cerein 7B, respectively, and identifies in large bold letters the sequences included in Table 2 and their location.

Figure 5:
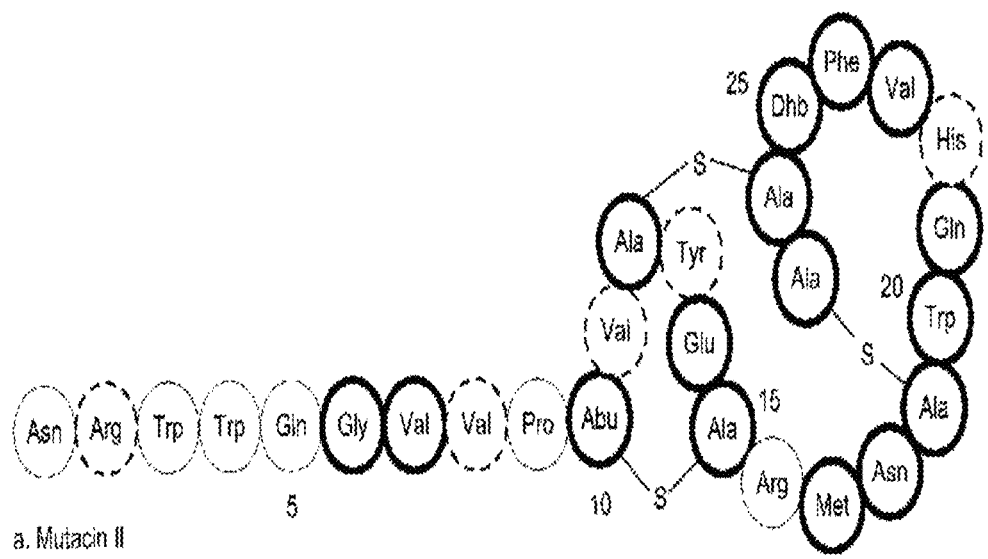
FIG. 5 is an exemplary illustration of the sequence of Mutacin II.

For example, for identification of peptides for *Corynebacterium* and *Micrococcus* Recognition sequences for *Staphylococcus aureus* and *Pseudomonas aeruginosa* can be found in the literature, but there were no sequences for *Corynebacterium* or *Micrococcus*. To identify potential sequences, bacteriocins that were selective for the two species and whose folding structure and sequences were known were used as a template. FIG. 5 shows one of the bacteriocins with its proposed structure. All of the bacteriocins examined had similar folding structures. The recognition sequence for this structure type has been reported as located at either the N terminal or the second loop. Using the three different bacteriocins (FIGS. 4A, 4B and 4C), six potential peptides taken from the N terminal and the second loop were synthesized and screened for bind as described previously. FIG. 5 includes the structure of the bacteria Mutacin II. The recognition sequence for the bacteriocins (FIGS. 4A, 4B and 4C) with this type of structure can be found at the N terminal (residue 1-10) or the second loop (residue 19-26 for this figure).

One embodiment includes a method of applying and binding an antimicrobial composition, e.g., PHMB, is a dip press-coating protocol. This protocol begins by immersing the textile to be coated in a solution of the antimicrobial composition, e.g., PH-MB and letting it sit with agitation for 2-6 hr. After removal from the solution of the antimicrobial composition, e.g., PHMB, excess liquid can then be removed from the immersed textile material by pressing the material, for example, between two rollers. The coated and pressed textile material can then be cured by heating the material at about 120° C. for 10 min. The concentration of PHMB in the solution in which the textile is immersed can range from about 0.00018% to about 2.5% (or about 0.18 ug/g to about 2.5 mg/g) depending on the species for which the antimicrobial is intended to kill. The solution concentration for most organisms that the PHMB is intended to kill can be from about 0.0031 to about 0.008% (or about 3.1 ug/g to about 8 ug/g).

Other embodiments include methods for attaching the peptide alone or the peptide after the PHMB is attached using the dip press coating method above using an EDC coupling reaction. For the EDC reaction used to attach the peptide alone, the EDC reaction for peptide attachment can be performed in a continuous process after the dip press coating method is used to attach the PHMB.

Other embodiments can include attaching the peptide to a fabric or textile that can be obtained and already include an antimicrobial composition attached thereto including the following examples: Cotton, Nylon, Polyester, rayon, etc.

The EDC coupling reaction being used to attach the peptide alone after the antimicrobial composition is attached and includes the following: submerge the swatches of the antimicrobial treated fabric into a dish of citric acid buffer (7% citric acid, 5% Sodium Hypophosphate monohydrate [SHP]); agitate, e.g., leave on shaker plate, for 1 hour at room temperature (about. 70° F./20° C.); cure by placing the still wet fabric on a paper towel in the microwave and microwave the fabric for 2 minutes (depending on the size of the fabric), making sure the fabric is on the outside edge of the microwave to prevent it from burning and ensuring the glass plate is in the microwave rotates the fabric throughout the curing process giving an even curing across the entire piece of fabric, after curing, the fabric is then washed in deionized water for about 10 minutes and agitated, for example, on a shaker plate; then the water is removed and a solution is added of 1-ethyl-3-[3-dimethylaminopropyl] carbodiimide hydrochloride (EDC solution at a concentration of amount 0.6372 g/30 ml (137 mM), in 200 mM monobasic sodium phosphate buffer) and it is agitated, e.g., on a shake plate, for about 45 minutes; and then the EDC solution from the previous step is removed and the fabric is then rinsed in about 20 mM sodium phosphate buffer pH 7.2 for about 5 minutes.

To attach the peptide and PHMB to the fabrics from 0037 a PHMB solution is prepared at a concentration noted above, (e.g., PHMB solution in about 20 mM Sodium Phosphate buffer); the PHMB solution is placed in a dish along with the peptide at a desired concentration; the fabric to be treated is placed in the dish and the dish allowed to incubate with agitation for about 2.5 hr.; the fabric is then washed in 20 mM phosphate buffer 5 min, then wash for 5 min in water; and after washing the fabric is then allowed to air dry.

Materials

Polyhexamethylene Biguanidine (PHMB) obtained from Arch Chemicals Norwalk, Conn. Peptides were synthesized by New England Peptide, Gardner, Mass. (Table 3). Fluorescein isothiocyanate (FITC) labeled peptide synthesized by Peptide 2.0, Chantilly, Va. Nutrient Broth, Mannitol Salts media, Triton X100, DE broth 1-Ethyl-3-(3-dimethylaminopropyl)carbodiimide (EDAC) were obtained from VWR, Radnor, Pa.

TABLE 3

| Sequence synthesized | Microorganism recognized |
|---|---|
| GGSGGSYSTCDFIM (AgrD1 pheromone) | Staphylococcus aureus |
| GGSGGSKKHRKEIRKEIRKH | Pseudomonas aeruginosa |
| GGSGGNGVVLTL | Corynebacterium and Micrococcus luteus |
| GGSGGTWTKKLK | Corynebacterium and Micrococcus luteus |
| GGSGGNRWWQGVVP | Corynebacterium and Micrococcus luteus |
| GGSGGSWQHVFT | Corynebacterium and Micrococcus luteus |
| GGSGGGWWNSWGKCV | Corynebacterium and Micrococcus luteus |
| GGSGGIGGVSGGLTG | Corynebacterium and Micrococcus luteus |

Table 3 list of peptide synthesized and tested with the organism they bind.

Procedures

Preparing Swatches

Peptides were synthesized at New England peptides with the linker sequence of GGSGGS or GGSGG on the N terminal (Table 1). Textile swatches of cotton or cotton-nylon blends were cut to 1 cm circles and the surface hydroxyls were converted to carboxyl by submerging the swatches 1 hour with agitation at 300 rpm in 25 mL of citric acid buffer (7% citric acid, 5% Sodium Hypophosphate monohydrate). (Synthetic material such as nylon and polyester require a pretreatment with sodium hydroxide before the citric acid buffer is added) To cure the reaction, the swatches were heated in a microwave for 2 minutes. After curing, swatches were washed the in 25 mL of deionized water for 5 min. The swatches were activated by submerging in 30 mL of EDC solution (0.6372 g in 30 mL 200 mM monobasic sodium phosphate buffer pH) and incubating for 45 minutes with 300 rpm agitation. After incubation, swatches were rinsed in 25 mL 20 mM sodium phosphate buffer pH 7.2 for 5 minutes. During the wash, 5 ml peptide samples were prepare from a 2 mg/ml stock of peptide in 20 mM sodium phosphate solution at concentrations of 2.5 or 1.25 mg/g peptide. The buffers were prepared with PHMB concentrations 0.031, 0.015, or 0.0075%. Each solution was added to one well of a six well microtiter plate. Swatches were added to one of the peptide/PHMB concentration solutions and incubated with agitation for 2.5 hr. Swatches were washed in 20 mM phosphate buffer for 5 min, then wash for 5 min in water twice and allowed to air dry.

Inoculum Prep

Inoculation took place using an 8 ml overnight cultures for each target microorganisms in appropriate media. For Staphylococcus aureus, Staphylococcus epidermidis and Pseudomonas aeruginosa cultures were grown on Nutrient broth. For Corynebacterium jeikieson the media was Brain Heart Infusion supplemented with 0.1% Tween 80 and for Micrococcus luteus the media was Brain Heart Infusion media. The OD for each culture was taken and diluted to an OD of 1 using appropriate growth media. For each culture a 1 mL aliquot was taken and transfer to a clean 2 mL eppendorf tube. The tubes were placed into a micro centrifuge and spun at 10,000 G until a pellet has formed. The media was aspirated without disturbing the pellet and the pellet was re-suspend in 1 mL of 0.125× Nutrient Broth with 0.15% Triton X-100. This was repeated to wash pellets. The pellet was re-suspend in 1 ml of 0.125× Nutrient Broth with 0.15% Triton X-100 and the above centrifugation was performed again. After last wash, the pellet was re-suspended in 1 ml of 0.125× Nutrient Broth with 0.15% Triton X-100 then added to 8 mL of 0.125× Nutrient Broth with 0.15% Triton X-100. This was the inoculum and should have had a final concentration of $10^7$-$10^8$ CFU/mL for each species inoculum. The inoculum was enumerated by adding 500 ul into 4.5 ml of PBS and serial diluting 7 more times. Counts were taken by spread plating only $10^{-6}$, $10^{-7}$ and $10^{-8}$.

Procedure for Testing Swatches for Binding and Antimicrobial Activity

Swatches prepared previously were inoculated with 25 ul of the inoculum (scoured samples will be used as a negative control). The inoculated swatches were incubated for 24 hr at 37° C. in a sealed tube. To analyze binding, the swatches were placed into 2.5 ml modified DE broth and vortex for 5 min. The modified DE broth was serial diluted $10^{-3}$ by adding 500 ul to 4.5 ml phosphate buffer. The dilution was spread plated onto the appropriate growth media (mannitol salts for Staphylococcus aureus, nutrient agar for Staphylococcus epidermidis, Cetrimide agar for Pseudomonas aeruginosa, Brain heart infusion for Micrococcus luteus and Brain Heart infusion with 0.1% Tween 80 for Corynebacterium jeikeium) and incubate overnight. Any developed colonies were counted and if there was PHMB the log kill was calculated using the scoured samples for a zero.

Determining Kill Vs Binding

Swatches of NyCo were prepared with 0 and 2.5 mg/ml of peptide and with and without 0.0017% PHMB. They were inoculated with 25 ul of Staphylococcus aureus 27217 or Staphylococcus aureus 25923 inoculum prepared as previously described. Swatches were incubated for 24 hr then placed into mannitol salts broth and incubated for another 24 hr to determine viability of bound cells. All sets were incubated at 37° C. Growth of organism was indicated by a media color change from red to yellow and signified viability of the *Staphylococcus aureus*. Any growth will be recorded. The results show that the swatch with the peptide and no PHMB show growth in the mannitol salts broth while the swatches with PHMB showed no growth. One surprising result was the 0 peptide, 0 PHMB controls did not show growth after 24 hr, though growth was evident after 48 hr incubation. No growth was seen in tubes with peptide and PHMB even after incubation for 48 hr.

Establishing Initial Concentration for Peptide and PHMB

The JMP design of experiment program from SAS was used to design the experiments. A preliminary experiment measured the textile MIC for PHMB against the different microorganisms applied using the dip press method currently used by industry. The numbers are listed in Table 4. These numbers were used for establishing PHMB concentration ranges for the binding experiments.

TABLE 4

| Microorganism | MIC applied using dip press |
|---|---|
| *Staphylococcus aureus* | 39 ug/ml or 0.0039% |
| *Staphylococcus epidermidis* | 39 ug/ml or 0.0039% |
| *Pseudomonas aeruginosa* | 20 mg/ml or 20% |
| *Corynebacterium jeikeium* | 312 ug/ml or 0.0312% |

Table 4 List of textile minimum inhibitory concentration for different skin microorganism.

Evaluating the Application Order for the Peptide and PHMB

Figure 6:
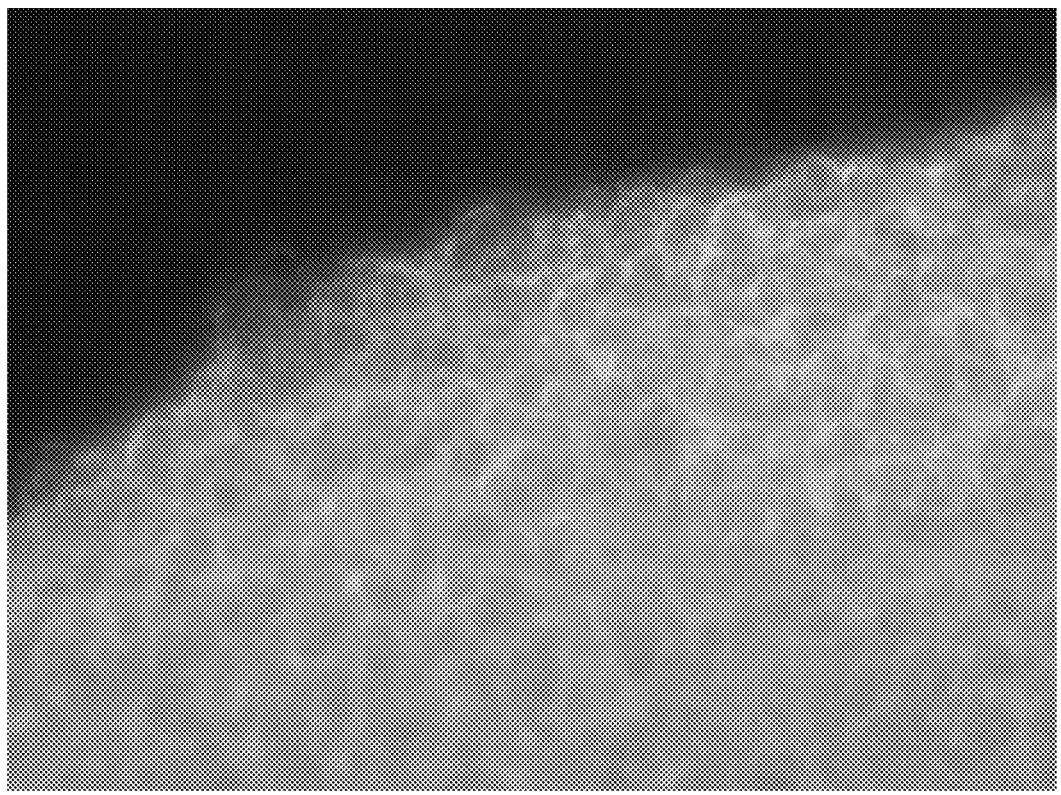
FIG. 6 is a photomicrograph of a textile surface with fluorescent labelled peptide bound at the same time as PHMB.
Figure 7:
FIG. 7 is a photomicrograph of a textile surface with fluorescent labelled peptide bound to surface after the PHMB was bound.

Another preliminary experiment for this effort established the application order for the peptide and PHMB. Experiments using FITC labelled peptide bound the peptides to NyCo surfaces when the PHMB was applied before peptide binding, after peptide binding and simultaneously. Peptide concentrations of 0, 5, 10 and 25 mg/ml were evaluated. The fabrics were visualized on a fluorescence microscope and antimicrobial activity was measured for the PHMB. The image seen is FIG. 6 shows the fluorescence when the peptide and the PHMB were applied simultaneously using the EDC reaction. Notice individual fibers can be seen suggesting the peptide is bound only to the fibers. The image in FIG. 7 shows when the PHMB was applied first using the dip press method with the peptide being bound after using the EDC reaction. In this image the individual fiber are not as clearly seen suggesting the peptide maybe binding to the PHMB instead of eth fibers. The antimicrobial results demonstrated the PHMB remained active for all samples, though there was a decrease in activity when the peptide is applied after the PHMB was attached supporting the theory that the peptide may bind to the active site for the PHMB. The fluorescence intensity for the different peptide concentration could not be distinguished for samples with peptide concentration of 5 mg/ml or above.

Evaluating Peptide Binding *Staphylococcus aureus*

The initial experiments set the peptide concentration at 0, 1.75 and 2.5 mg/ml with the PHMB concentration of 0.0031, 0.0017, 0.0008 and 0% using the peptide which binds *Staphylococcus aureus*. These concentration were chosen based upon result from previously described experiments. The treated fabric was evaluated against two different strains of *Staphylococcus aureus* (Table 5). For both strains, peptide concentration of 2.5 mg/ml completely bound all of the cells regardless of the PHMB concentration. The lower peptide concentrations may have bound some of the cells, but not all of them. This suggest the lowest peptide concentration that will bind the cells is 2.5 mg/ml and will be used for future experiments. The 0.0031% PHMB killed all the cells regardless of the peptide concentration which was unexpected. The preliminary MIC results showed that 0.0039% was the lowest concentration necessary to kill the *Staphylococcus aureus*. The 0.0031% concentration is lower and may suggest that the EDC reaction allows for a greater amount of PHMB to be bound to the surface of the fabric over the traditional Dip Press method. A follow up experiment provide additional evidence for this possibility.

TABLE 5

| Peptide Conc | 0 mg/g | 1.75 mg/g | 2.5 mg/ml | 0 mg/g | 1.75 mg/g | 2.5 mg/ml |
|---|---|---|---|---|---|---|
| | PHMB conc | | | | | |
| | 0% | | | 0.0008 | | |
| *S aureus* 27217 | 544375 | 475000 | 0 | 24833 | NA | 0 |
| *S. aureus* 25923 | 2119400 | 4765000 | 0 | 140000 | NA | 0 |
| | PHMB conc | | | | | |
| | 0.0017 | | | 0.0031 | | |
| *S. aureus* 27217 | 8150 | 5410 | 5000 | 0 | 0 | 0 |
| *S. aureus* 25923 | 5300 | 11200 | 0 | 0 | 0 | 0 |

Table 5 results from antimicrobial evaluation of *Staphylococcus aureus*.

Evaluating Peptide Binding *Staphylococcus aureus* and *Staphylococcus epidermidis*

An experiment was run using the same two *Staphylococcus aureus* strains 27217 and 25923 with the addition of *Staphylococcus epidermidis*. The PHMB concentration was dropped to 0.0008% which should be well below the new MIC. The results are recorded in Table 6. When the peptide is present, no *Staphylococcus aureus* cell were recovered. This is in contrast to *Staphylococcus epidermidis* where there does not appear to be any binding by the peptide showing a preferential binding toward one species over another. One interesting result for the *Staphylococcus epidermidis* is the lack of cells recovered when the PHMB is present without peptide, but there were cells recovered when there is PHMB and peptide present. This suggests a binding competition between the peptide and the PHMB during the EDC reaction. This is similar to the previous study where it appears that when PHMB alone is applied using the EDC reaction, there is more PHMB bound to the surface. But when the PHMB is applied with peptide using the EDC reaction the PHMB bound to the surface is lower.

TABLE 6

| | PHMB conc | | | |
|---|---|---|---|---|
| | 0% | | 0.0008% | |
| Peptide Conc | 0 mg/ml | 2.5 mg/ml | 0 mg/ml | 2.5 mg/ml |
| *S aureus* 27217 | 544375 | 0 | 24833 | 0 |
| *S. aureus* 25923 | 2119400 | 0 | 140000 | 0 |
| *S. epidermidis* 12228 | 729000 | 693000 | 0 | 387000 |

Table 6 Results for PHMB concentration of 0 and 0.0008% along with 2.5 mg/ml peptide.

Evaluating Peptide Binding *Pseudomonas aeruginosa*

*Pseudomonas aeruginosa* was examined using concentrations based upon the textile MIC. The sequence GGSGG-SKKHRKHRKHRKH was bound to the textile at 0 mg/ml and 2.5 mg/ml with early experiments using PHMB concentrations of 20, 15, 5 and 2.5% as determined from previous MIC studies. The results are recorded in Table 7.

Evaluating Peptide Binding *Pseudomonas aeruginosa*

The six potential peptides were attached to swatches and exposed to *Corynebacterium jeikeium, Micrococcus luteus, Staphylococcus epidermidis, Staphylococcus aureus* and *Pseudomonas aeruginosa*. The results can be seen in Table 9.

TABLE 9

| Sample | C. Jeikeium | M luteus | S. epidermidis | S. aureus | P. aeruginosa |
|---|---|---|---|---|---|
| no peptide | TNTC | 1825000 | 5670000 | 6920000 | TNTC |
| GGSGGNGVVLTL (Cj 1) | 175 | 0 | 65500 | 6055000 | 40000 |
| GGSGGTWTKKLK (Cj2) | 0 | 0 | 294000 | 7680000 | TNTC |
| GGSGGNRWWQGVVP (Cj3) | 300 | 0 | 121500 | 7040000 | 27000 |
| GGSGGSWQHVFT (Cj 4) | 245 | 0 | 145000 | 5315000 | 28000 |
| GGSGGGWWNSWGKCV (Cj 5) | 0 | 0 | 337000 | 4195000 | TNTC |
| GGSGGIGGVSGGLTG (Cj 6) | 0 | 0 | 122000 | 5980000 | 175000 |

TABLE 7

| Sample | CFU |
|---|---|
| 0 pep, 0% PHMB | 4900000 |
| 2.5% PHMB | 0 |
| 5% PHMB | 0 |
| 0 pep, 10% | 0 |
| 0 pep, 15% | 0 |
| 2.5 pep, 0% | 0 |
| 2.5 pep, 10% | 0 |
| 2.5 pep, 15% | 0 |

Table 7 Results of Recognition Sequence for PA

The no PHMB no peptide result confirm that the *Pseudomonas aeruginosa* does not bind to the fabric and can be recovered. But no cells were recovered for any other swatch. This was expected for the swatches that had peptide, but the no peptide with PHMB results are similar to what was seem for the *Staphylococcus aureus* results where the EDC reaction provides a greater surface coverage of the PHMB that the textile MIC changes.

Swatches with PHMB ranges of 5, 2.5, 1.25, 0.625, 0.312, 0.156, 0.078, 0.039, 0.0195, 0.00975, 0.00487 and 0.00248% were prepared and tested for killing of *Pseudomonas aeruginosa*. The results are in table 8. The results show a MIC closer to the results seen for *Staphylococcus aureus* and suggest a significantly higher PHMB surface coverage than what was seen for the standard dip press method.

TABLE 8

| PHMB | CFU |
|---|---|
| 0 | 4900000 |
| 5 | 0 |
| 2.5 | 0 |
| 1.25 | 0 |
| 0.625 | 0 |
| 0.312 | 0 |
| 0.156 | 0 |
| 0.078 | 0 |
| 0.039 | 0 |
| 0.01950 | 60 |
| 0.00975 | 15 |
| 0.00487 | 2350 |
| 0.00248 | 3200 |

Table 8 Results for MIC tests pf EDC applied PHMB.

Table 9 Results for the six potential *Corynebacterium* and *Micrococcus* recognition peptides.

The results show complete binding of the *Micrococcus luteus* by all six peptides and partial or complete binding for the *Corynebacterium jeikieum*. Little to no binding was observed by the other species examined. Though it was expected that there would be some binding by the peptides against the target species, the level of binding was unexpected and encouraging. In addition, the lack of binding by the other skin microorganism was promising.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. A method of treating a fabric to selectively kill bacteria, comprising: binding an antimicrobial composition and a peptide to the fabric, wherein the peptide is selected from the group consisting of:

GGSGGSYSTCDFIM; (SEQ ID NO: 7)

GGSGGSKKHRKHRKHRKH; (SEQ ID NO: 8)

GGSGGNGVVLTL; (SEQ ID NO: 1)

GGSGGTWTKKLK; (SEQ ID NO: 2)

GGSGGNRVVWQGVVP; (SEQ ID NO: 3)

GGSGGSWQHVFT; (SEQ ID NO: 4)

GGSGGGVVWNSWGKCV; (SEQ ID NO: 5)

GGSGGIGGVSGGLTG; (SEQ ID NO: 6)

and

GGSGGSYSTCYFIM; (SEQ ID NO: 9)

and wherein the binding step includes binding the antimicrobial composition before binding the peptide.

2. The method of claim 1, wherein the antimicrobial composition is polyhexamethylene biguanidine (PHMB).

3. The method of claim 1, wherein the fabric includes an antimicrobial surface and the antimicrobial composition and the peptide are bound to the antimicrobial surface.

4. The method of claim 1, wherein binding the antimicrobial includes using a dip press-coating protocol or an EDC coupling reaction.

5. The method of claim 1, wherein binding the peptide includes using an EDC coupling reaction.

6. The method of claim 1, wherein the peptide binds to and the antimicrobial composition kills odor causing or pathogenic bacteria.

7. The method of claim 1, wherein the peptide selectively binds to at least one bacteria of *Staphylococcus aureus*, *Pseudomonas aeruginosa*, *Corynebacterium* and *Micrococcus luteus* and the antimicrobial composition kills at least one bacteria.

* * * * *